[19] United States Patent
Tahara et al.

[11] 3,952,006
[45] Apr. 20, 1976

[54] THIOPHENE DERIVATIVES

[75] Inventors: Tetsuya Tahara; Hideo Matsuki; Kazuhiko Araki; Masami Shiroki, all of Yoshitomi, Japan

[73] Assignee: Yoshitomi Pharmaceutical Industries, Ltd., Osaka, Japan

[22] Filed: Aug. 8, 1973

[21] Appl. No.: 386,819

[30] Foreign Application Priority Data
Aug. 8, 1972 Japan................................ 47-79809
Aug. 30, 1972 Japan............................... 47-87242
Sept. 13, 1972 Japan............................... 47-92534
Sept. 16, 1972 Japan............................... 47-93337

[52] U.S. Cl. .................. 260/309; 260/247.1 M; 260/268 MK; 260/268 FT; 260/293.68; 260/308 R; 260/308 D; 260/329 F; 424/248; 424/250; 424/267; 424/269; 424/273
[51] Int. Cl.² ..................................... C07D 417/04
[58] Field of Search ........ 260/308 R, 309, 247.1 M, 260/268 FT, 293.68, 268 MK

[56] References Cited
UNITED STATES PATENTS
3,609,959   6/1972   Hromatka et al. ............. 260/239.3 B
3,763,179   10/1973  Gall .................................. 260/309

FOREIGN PATENTS OR APPLICATIONS
2,107,356   8/1971   Germany..................... 260/239.3 B Primary Examiner—R. Gallagher
Attorney, Agent, or Firm—Sughrue, Rothwell, Mion, Zinn & Macpeak

[57] ABSTRACT

Thiophene derivatives of the formula:

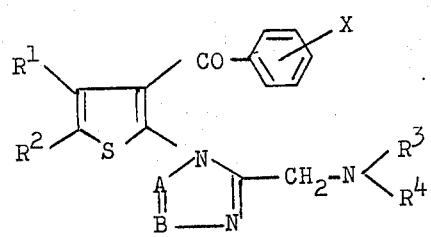

wherein $R^1$ is H or $CH_3$; $R^2$ is $CH_3$ or $C_2H_5$, or $R^1$ and $R^2$ combinedly represent $-(CH_2)_4-$; each of $R^3$ and $R^4$ is H, alkyl of from 1 to 4 carbon atoms or cyclohexyl, or $R^3$ and $R^4$ together with the adjacent nitrogen atom form 1-pyrrolidinyl, piperidino, 4-methyl-1-piperazinyl or morpholino; X is H, halogen or $OCH_3$; A is $-CH=$ or $-C(CH_3)=$, and B is $=N-$ or $=CH-$; or A is $-C(CH_2OH)=$ or $-N=$, and B is $=N-$, and pharmaceutically acceptable acid addition salts thereof possess excellent pharmacological properties such as sedative, anxiolytic and anticonvulsant effects and protective effects against hypoxia or anoxia.

6 Claims, No Drawings

THIOPHENE DERIVATIVES

This invention relates to novel and therapeutically valuable compounds of the formula

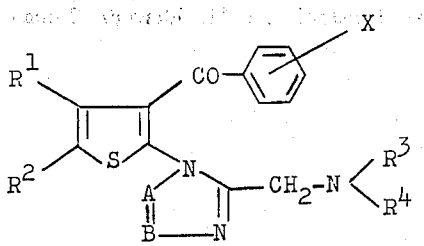

(I)

and pharmaceutically acceptable acid addition salts thereof. In the above formula, $R^1$ is H or $CH_3$; $R^2$ is $CH_3$ or $C_2H_5$, or $R^1$ and $R^2$ combinedly represent $-(CH_2)_4-$; each of $R^3$ and $R^4$ is H, alkyl of from 1 to 4 carbon atoms or cyclohexyl, or $R^3$ and $R^4$ together with the adjacent nitrogen atom form 1-pyrrolidinyl, piperidino, 4-methyl-1-piperazinyl or morpholino; X is H, halogen or $OCH_3$; A is $-CH=$ or $-C(CH_3)=$, and B is $=N-$ or $=CH-$; or A is $-C(CH_2OH)=$ or $-N=$, and B is $=N-$.

The compounds of the general formula (I) can be produced by one of the following methods (a) to (c).

a. In the case of the compounds of formula (I) wherein A is $-CH=$, $-C(CH_3)=$ or $-N=$, by reacting a compound of the formula

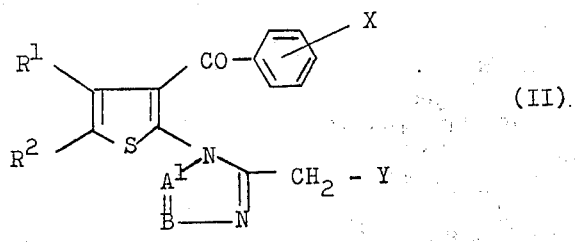

(II)

wherein Y is halogen, arylsulfonyloxy or alkylsulfonyloxy, $A^1$ is $-CH=$ or $-C(CH_3)=$, and B is $=N-$ or $=CH-$, or A is $-N=$, and B is $=N-$, and other symbols are as defined above, with a compound of the formula

(III)

wherein $R^3$ and $R^4$ are as defined above.

The reaction is usually carried out in the presence of a solvent such as an alcohol (e.g. methanol, ethanol, propanol, 2-propanol, butanol), a ketone (e.g. acetone, methyl ethyl ketone, cyclohexanone), an aromatic hydrocarbone (e.g. benzene, toluene, xylene), a halogenated hydrocarbone (e.g. chloroform, dichloromethane, dichloroethane, chlorobenzene), an ether (e.g. diethyl ether, dibutyl ether, tetrahydrofuran, dioxane), pyridine, dimethylformamide or dimethylsulfoxide, advantageously in the presence of a deacidifying agent such as an alkali hydroxide (e.g. NaOH, KOH), an alkali carbonate (e.g. $Na_2CO_3$, $NaHCO_3$, $K_2CO_3$) or a tertiary amine (e.g. pyridine, triethylamine), at a temperature of from room temperature to a refluxing temperature of the solvent employed for a period of from 0.5 to 48 hours. An excess of the compound of formula (III) may also serve as a deacidifying agent. The reaction, if desired, may also be carried out in an autoclave without solvent.

b. In the case of the compounds of formula (I) wherein $R^3$ and $R^4$ are H, and A is $-CH=$, $-C(CH_3)=$ or $-N=$, by hydrolyzing a compound of the formula

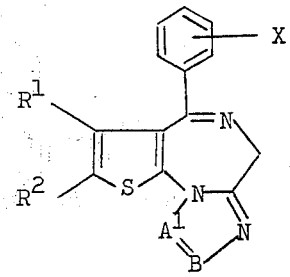

(IV)

wherein each symbol is as defined above.

The hydrolysis is carried out in an aqueous medium in the presence of an inorganic acid (e.g. hydrochloric, sulfuric, phosphoric acid) or an organic acid (e.g. p-toluenesulfonic, methanesulfonic acid) at a pH below 5 and at a temperature of from room temperature to a boiling point of the solvent employed, for a period of from 0.5 to several hours. The aqueous medium may contain a solvent such as methanol, ethanol, dimethylformamide, dioxane or tetrahydrofuran for the dissolution of compound (IV).

c. In the case of the compounds of formula (I) wherein $R^3$ and $R^4$ are both $CH_3$: by reacting a compound of formula (IV) or a compound of the formula:

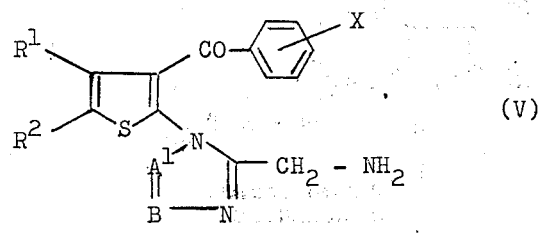

(V)

wherein each symbol is as defined above, with formic acid and formaldehyde.

The amounts of formic acid and formaldehyde to be used are each about 2 to 10 moles, preferably about 3 to 5 moles, per mole of a compound of formula (IV) or (V), the molar ratio of formic acid and formaldehyde being preferably about 1:1 to 1:1.2. This reaction is carried out by heating under reflux for a period of from 1 to 24 hours, optionally in the presence of an inert organic solvent such as methanol, ethanol, tetrahydrofuran, dioxane, benzene or dimethylformamide. In the case of the compounds of formula (V) wherein $-A^1=B-$ is $-CH=N-$, when this reaction is carried out for a long period of time (e.g. over 3 hours), an excess of formaldehyde acts upon the hydrogen atom of $A^1$ to give a compound of formula (I) wherein $-A=B-$ is $-C(CH_2OH)=N-$.

The compounds of formula (I) can be converted into acid addition salts with various inorganic acids (e.g.

hydrochloric, hydrobromic, nitric, sulfuric, phosphoric acid) or with various organic acids (e.g. formic, acetic, oxalic, maleic, fumaric, tartaric, methanesulfonic, p-toluenesulfonic, camphor-β-sulfonic acid).

The starting compounds of formula (IV) can be prepared, for example, by the methods representable by the following scheme:

Specific examples of the preparation of the starting compounds of formulae (IV'), (IV'') and (IV''') are as follows:

1. Preparation of Starting Compound of Formula (IV')

[a] To a solution of 40 g of 5-o-chlorophenyl-7-ethyl-1,2-dihydro-3H-thieno[2,3-e][1,4]diazepin-2-one in

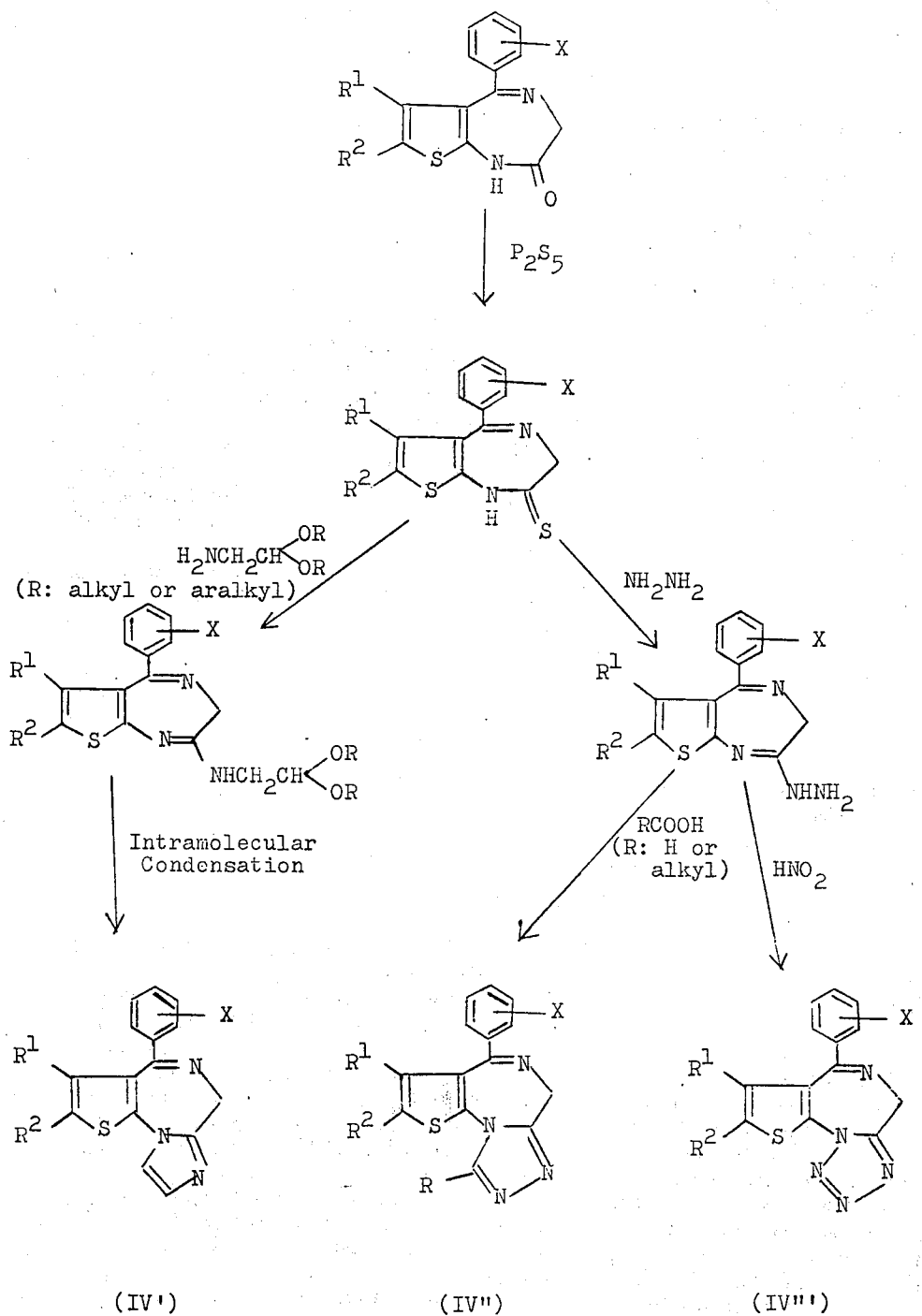

200 ml of pyridine is added 32 g of phosphorus pentasulfide, and the mixture is stirred at 60°C for 1 hour. After allowing to cool, the reaction mixture is poured into 2 liters of ice water with stirring. The precipitate formed is collected with suction filtration and washed with water. The precipitate is dissolved in chloroform, and the solution is washed with a saturated sodium bicarbonate and washed with water. The chloroform layer is dried over sodium sulfate and concentrated in vacuo. The residue is recrystallized from a mixture of ethanol and chloroform to give 31.4 g of 5-o-chlorophenyl-7-ethyl-1,2-dihydro-3H-thieno[2,3-e][1,4]diazepine-2-thione as yellowish crystals melting at 198°–199°C (decomposition).

[b] A mixture of 20 g of 5-o-chlorophenyl-7-ethyl-1,2-dihydro-3H-thieno[2,3-e][1,4]diazepine-2-thione and 9.6 g of aminoacetaldehyde diethylacetal is added to 200 ml of ethanol, and the whole mixture is refluxed for 2.5 hours. While the reaction mixture is hot, an activated carbon is added to the reaction mixture. The whole mixture is filtered and the filtrate is cooled. The crystals formed are collected by suction filtration and washed with a small amount of ethanol to give 23 g of 5-o-chlorophenyl-2-(2,2-diethoxyethylamino)-7-ethyl-3H-thieno[2,3-e][1,4]diazepine melting at 143° – 146°C.

[c] A solution of 7.0 g of 5-o-chlorophenyl-2-(2,2-diethoxyethylamino)-7-ethyl-3H-thieno[2,3-e][1,4]diazepine in 60 ml of glacial acetic acid is refluxed moderately for 2 hours. After cooling, the acetic acid is distilled off under reduced pressure. The residue is made alkaline with an aqueous sodium carbonate solution, and the solution is extracted with ethyl acetate. The extract is washed with water, dried over sodium sulfate, and concentrated in vacuo. to the viscous oil obtained is added a mixture of ligroin and ethyl acetate (9:1), and the crystals formed are collected by suction filtration. The crystals (5.1 g) are recrystallized from a mixture of ligroin and ethyl acetate (9:1) to give 6-o-chlorophenyl-8-ethyl-4H-imidazo[2,1-c]thieno[2,3,-e][1,4]diazepine as colorless plates melting at 124° – 127°C.

2. Preparation of Starting Compound of Formula (IV'')

[d] 32.1 g of 5-o-chlorophenyl-7-ethyl-1,2-dihydro-3H-thieno[2,3-e][1,4]diazepine-2-thione obtained in the above example [a] is suspended in 200 ml of ethanol, and to the suspension is added 8 g of hydrazine hydrate. Several minutes stirring turns the suspension into a homogeneous, red, transparent solution. Then crystals begin to precipitate. After stirring at room temperature for 2 hours and subsequent ice-cooling, the crystals are collected by suction filtration and washed well with methanol to give 28.6 g of almost pure 2-hydrazino-5-o-chlorophenyl-7-ethyl-3H-thieno[2,3-e][1,4]diazepine as yellowish crystals. The crystals, when recrystallized from a mixture of ethanol and diemethylformamide, show a melting point of 214° – 216°C (decomposition).

[e] A mixture of 3.2 g of 2-hydrazino-5-o-chlorophenyl-7-ethyl-3H-thieno[2,3-e][1,4]diazepine and 20 ml of formic acid is allowed to stand overnight at room temperature. The mixture is poured into 300 ml of ice water and neutralized with sodium bicarbonate. The mixture neutralized is extracted with ethyl acetate, and the ethyl acetate layer washed with a saturated aqueous sodium chloride solution, dried over sodium sulfate and concentrated in vacuo. The residue is recrystallized from a mixture of ligroin and ethanol to give 2.1 g of 6-o-chlorophenyl-8-ethyl-4H-s-triazolo[3,4-c]thieno[2,3-e][1,4]diazepine as colorless needles melting at 153° – 154°C.

3. Preparation of Starting compound of Formula (IV''')

[f] 10 g of 2-hydrazino-5-o-chlorophenyl-7-ethyl-3H-thieno[2,3-e][1,4]diazepine prepared in the above example [d] is suspended in 54 ml of 2N hydrochloric acid. A solution of 2.4 g of sodium nitrite in 20 ml of water is added to the suspension at −5°C with stirring. The mixture is stirred at room temperature for 30 minutes, and then alkalified with sodium carbonate. The precipitated crystals are filtered off and dissolved in chloroform, and the solution is washed with water. The chloroform layer is dried over anhydrous magnesium sulfate, and the chloroform is distilled off under reduced pressure. The reddish brown jellylike residue thus obtained is crystallized from a mixture of ligroin and ethanol to give 8.2 g of 6-o-chlorophenyl-8-ethyl-4H-tetrazolo[5,1-c]thieno[2,3-e][1,4]diazepine as white crystals. The product, when recrystallized from ethanol, melts at 135° – 136°C.

The starting compounds of formula (II) can be prepared by the following methods:

[i] A compound of formula (IV) is hydrolyzed in the presence of a hydrohalogenic acid (e.g. HCl, HBr) in an inert solvent such as water, methanol, ethanol, 2-propanol, butanol acetone, benzene, dioxane, tetrahydrofuran, dimethylformamide or acetic acid at a temperature of from room temperature to a refluxing temperature of the solvent employed for a period of from 0.5 to 20 hours. The resulting hydrolysis product is allowed to react with an alkali metal nitrite (e.g. NaNO$_2$, KNO$_2$) at a temperature of from room temperature to a refluxing temperature of the solvent employed for a period of from several minutes to several hours to give a mixture of compounds of formulae:

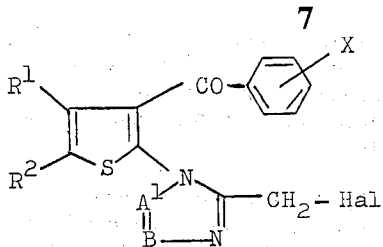
(II')

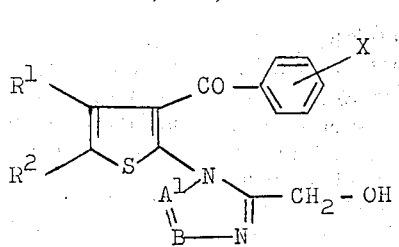
(VI)

wherein Hal is halogen, and other symbols are as defined above.

In the above reaction process, when the hydrolysis is carried out in the presence of an acid other than the hydrohalogenic acid, such as sulfuric acid, the compound of formula (VI) alone is obtained.

The compounds (II') and (VI) can be separated by liquid column chromatography on silica gel or alumina, or by the use of their different solubilities in a dilute inorganic acid, because the compound of formula (II') is only slightly soluble in a dilute inorganic acid, and the compound of formula (VI) is highly soluble in a dilute inorganic acid.

[ii] The compounds of formula (II) are also produced by reacting a compound of formula (VI) with a halogenating agent (e.g. thionyl chloride, phosphorus oxychloride, phosphorus pentachloride, phosphorus trichloride, phosphorus tribromide, hydrobromic acid - sulfuric acid, hydrochloric acid - zinc chloride) or a functional derivative of a sulfonic acid (e.g. arenesulfonyl chloride, alkanesulfonyl chloride, arenesulfonic (acid) anhydride, alkanesulfonic (acid) anhydride) with or without a solvent such as water, ether, dioxane, tetrahydrofuran, benzene, chloroform or pyridine at a temperature of from room temperature to a refluxing temperature of the solvent employed for a period of from several minutes to several hours. Specific examples are given in the following:

1. A solution of 10.8 g of 6-o-chlorophenyl-8-ethyl-4-H-imidazo[2,1-c]thieno[2,3-e][1,4]diazepine in 216 ml of 10% hydrochloric acid is refluxed with stirring for half an hour. After cooling, 2.2 g of sodium nitrite is added to the reaction mixture with stirring. The mixture is stirred at room temperature for half an hour, and then refluxed with stirring for half an hour. After cooling, 2.2 g of sodium nitrite is added to the reaction mixture. The whole mixture is stirred at room temperature for half an hour, and allowed to stand overnight. The yellowish oil formed is extracted with ethyl acetate. The ethyl acetate layer is washed with aqueous sodium bicarbonate, washed with water and dried over anhydrous magnesium sulfate. The ethyl acetate is distilled of under reduced pressure. The crude brown oil obtained is purified by chromatography on silica gel to give 2-chloromethyl-1-(3-o-chlorobenzoyl-5-ethyl-2-thienyl)imidazole as a yellowish oil ($n_D^{20} = 1.6061$).

2. a. A solution of 10 g of 1-methyl-6-o-chlorophenyl-8-ethyl-4H-1,2,4-triazolo[3,4-c]thieno[2,3-3][1,4]diazepine in 200 ml of 10% hydrochloric acid is heated under reflux for 2.5 hours. After cooling with ice, 5 g of sodium nitrite is added to the reaction solution, and the mixture is stirred at room temperature for 1 hour. To the mixture is added 500 ml of water, and the whole mixture is extracted with ethyl acetate. The ethyl acetate layer is washed with a sodium bicarbonate solution and dried over anhydrous sodium sulfate, and the solvent is distilled off. The residue is chromatographed over 200 ml of 70 – 325 mesh silica gel with a mixture of chloroform and methanol (250:1) as eluent. The eluate is concentrated in vacuo, and the residue is crystallized from ligroin and recrystallized from a mixture of ligroin and ethyl acetate to give 4.2 g of 3-chloromethyl-4-(3-o-chlorobenzoyl-5-ethyl-2 -thienyl)-5-methyl-4H-1,2,4-triazole as colorless pillars melting at 109° – 110°C.

b. In the above process, after extracting with ethyl acetate, the aqueous layer is made alkaline with potassium carbonate, and the alkaline solution is extracted with ethyl acetate. The extract is washed with water and dried over anhydrous sodium sulfate, and the solvent is distilled off. The crude crystals obtained are recrystallized from ethanol to give 3.4 g of 3-hydroxymethyl-4-(3-o-chlorobenzoyl-5-ethyl-2-thienyl)-5-methyl-4H-1,2,4triazole as colorless crystals melting at 140° – 141°C.

3. Four grams of thionyl chloride is added dropwise to a solution of 10 g of 3-hydroxymethyl-4-(3-o-chlorobenzoyl-5-ethyl-2-thienyl)-5-methyl-4H-1,2,4-triazole in 50 ml of dioxane. The mixture is stirred at 70° – 80°C for 2 hours. The reaction mixture is poured into 200 ml of water and made alkaline with potassium carbonate. The oil liberated is extracted with ethyl acetate. The extract is washed with water, dried over anhydrous sodium sulfate and concentrated in vacuo. The residue is treated with ligroin containing 5% ethyl acetate to cause crystallization. The crystals are collected by suction filtration and recrystallized from ligroin containing 5% ethyl acetate to give 9.3 g of 3-chloromethyl-4-(3-o-chlorobenzoyl-5-ethyl-2-thienyl)-5-methyl-4H-1,2,4-triazole as colorless pillars melting at 109° – 110°C.

4. To a solution of 4.5 g of 3-hydroxymethyl-4-(3-o-chlorobenzoyl-5-ethyl-2-thienyl)-5-methyl-4H-1,2,4-triazole in 50 ml of pyridine is added 2.5 g of tosyl chloride, and the mixture is allowed to stand at room temperature overnight. The solvent is distilled off, and the residue to which water is added is made alkaline with sodium bicarbonate and extracted with ethyl acetate. The ethyl acetate layer is dried over anhydrous sodium sulfate and the solvent is distilled off to give 3-tosyloxymethyl-4-(3-o-chlorobenzoyl-5-ethyl-2-thienyl)-5-methyl-4H-1,2,4-triazole as a yellowish oil.

The following compounds are prepared in an analogous manner:

3-chloromethyl-4-(3-o-chlorobenzoyl-5-methyl-2-thienyl)-5-methyl-4H-1,2,4-triazole, $n_D^{20} = 1.6006$;

3-chloromethyl-4-(3-o-chlorobenzoyl-5-ethyl-2-thienyl)-4H-1,2,4-triazole, $n_D^{20} = 1.5930$;

3-chloromethyl-4-(3-o-fluorobenzoyl-5-ethyl-2-thienyl)-5-methyl-4H-1,2,4-triazole, $n_D^{20} = 1.5868$;

3-chloromethyl-4-(3-o-chlorobenzoyl-4,5-dimethyl-2-thienyl)-5-methyl-4H-1,2,4-triazole, $n_D^{20} = 1.5942$;

3-chloromethyl-4-(3-o-chlorobenzoyl-4,5,6,7-tetrahydro-[1]-benzothiophen-2-yl)-5-methyl-4H-1,2,4-triazole, melting at 128° – 130°C;

2-chloromethyl-1-(3-benzoyl-5-ethyl-2-thienyl)imidazole, $n_D^{20} = 1.6015$;

2-chloromethyl-1-(3-o-fluorobenzoyl-5-ethyl-2-thienyl)imidazole, $n_D^{20} = 1.5952$;

2-chloromethyl-1-(3-o-chlorobenzoyl-4,5-dimethyl-2-thienyl)imidazole, melting at 128° – 129°C.

The compounds of formula (I) and pharmaceutically acceptable acid addition salts thereof possess excellent pharmacological properties such as sedative, anxiolytic and anticonvulsant effects and protective effects against hypoxia or anoxia, as shown, for example, by the following tests:

Methods

(i) Suppression of Fighting Behavior

Fighting episodes were produced in mice by the method described by Tedeshi et al in Journal of Pharmacology and Experimental Therapeutics, vol. 125, pp. 28 ff. (1959). Groups of 8 female mice (4 pairs) were given orally the test compound 60 minutes prior to receiving electric foot-shock for 3 minutes with 530 volts interrupted direct current, 1.3 milliamperes, 10 Hertz. Those pairs which exhibited 3 fighting episodes or less within 3 minutes were deemed to be an suppressed effectively by the test compound. The control mice of 81 pairs had shown 8.7 fighting episodes on the average under the same conditions. The $ED_{50}$, a dose required to suppress 50% of fighting pairs, was determined graphically.

(ii) Anti-pentylenetetrazole Effect

Pentylenetetrazole (150 mg/kg) was administered subcutaneously to groups each of 6 mice 15 minutes after the intraperitoneal administration of the test compound. The number of dead mice was counted within 3 hours after the administration of pentylenetetrazole, and then the $ED_{50}$, a dose required to suppress the mortality rate to 50%, was determined graphically.

(iii) Protective Effect against Hypoxia

Groups each of 15 female mice were given intraperitoneally the test compounds 10 minutes before the test. Control animals were given the vehicle. Animals were placed in a chamber, of which the inside pressure was lowered to 210 mmHg. The survival time, the time interval between the induction of hypoxia and the cessation of respiration, was determined. The minimal effective dose (MED), a dose required to prolongate the survival time significantly compared with the control group, was assessed by Student's t test.

Results

| actions | compounds A | B | C | D |
|---|---|---|---|---|
| Suppression of Fighting Behavior $ED_{50}$(mg/kg) | 2.5–10 | 0.63–2.5 | 2.5–10 | 1.56 |
| Anti-pentylenetetrazole Effect $ED_{50}$ (mg/kg) | 1.25–5.0 | 1.25–5.0 | 1.25 | 0.45 |
| Protective Effect against Hypoxia MED (mg/kg) | 3.0 | 1.0 | 1.0 | 3.0 |

In the above Table, the test compounds (A, B, C and D) are as follows:

A: 1-(3-o-chlorobenzoyl-5-ethyl-2-thienyl)-2-dimethylaminomethylimidazole dihydrochloride B: 1-(5-ethyl-3-o-fluorobenzoyl-2-thienyl)-2-dimethylaminomethylimidazole dihydrochloride C: 1-(3-o-bromobenzoyl-5-ethyl-2-thienyl)-2-dimethylaminomethylimidazole oxalate D: 3-aminomethyl-4-(3-o-chlorobenzoyl-5-ethyl-2-thienyl)-5-methyl-4H-1,2,4-triazole di-paratoluenesulfonate In view of the tests including those mentioned above, the compounds of formula (I) and pharmaceutically acceptable acid addition salts thereof can be safely used in the treatment of neurotic conditions accompanied by anxiety and tension and convulsive states and as a sedative for pre-anesthetic medication. And further they can be safely used in the treatment of comatose patient with stroke or cerebral edema in cerebrovascular disorder, postepileptic coma, anoxia of the newborn and coma following chemicals poisoning.

They can be administered orally or parenterally in the form of a pharmaceutical preparation with a suitable and conventional pharmaceutically acceptable inert carrier or adjuvant, without adversely affecting the patient treated.

The pharmaceutical preparations can take any conventional form such as tablets, capsules, powders or injectable solutions.

Formulation Example 1. 5 mg and 10 mg tablets are prepared from the following compositions:

| | 5 mg Tablet | 10 mg Tablet |
|---|---|---|
| Compound (I) or its salts | 5.0 mg | 10.0 mg |
| Lactose | 62.3 mg | 57.3 mg |
| Corn Starch | 25.0 mg | 25.0 mg |
| Microcrystalline Cellulose | 6.0 mg | 6.0 mg |
| Methyl Cellulose | 1.0 mg | 1.0 mg |
| Magnesium Stearate | 0.7 mg | 0.7 mg |
| | 100.0 mg | 100.0 mg |

2. 1% injectable solution is prepared from the following composition:

| | |
|---|---|
| Compound (I) or its salt | 20 mg |
| Sodium Chloride | 18 mg |
| Water for Injection | A sufficient amount to make 2 ml |

The daily dose of compound (I) or a salt thereof for human adults usually ranges from about 10 to 60 mg, e.g. 1 to 6 tablets, each tablet containing 10 mg of the compound (I), in a single or multiple dose. However, the dose may vary with the age, body weight, diagnosis and response of the individual patient.

The present invention will be better understood from the following examples, which are merely intended to be illustrative and not limitative of the present invention.

EXAMPLE 1

A solution of 5.0 g of 1-methyl-6-o-chlorophenyl-8-ethyl-4H-s-triazolo-[3,4-c]thieno[2,3-e][1,4]diazepine in 50 ml of 10% hydrochloric acid is stirred on a water bath for 2 hours. After cooling with ice, the reaction solution is made slightly alkaline with potassium carbonate. The oil liberated is extracted with ethyl acetate and the extract is dried over anhydrous sodium sulfate. To the extract is added a solution of 5.0 g of p-toluenesulfonic acid in 5 ml of ethanol, and the mixture is allowed to stand for some time. The crystals formed are collected by filtration and recrystallized from a mixture of ethyl acetate and ethanol to give 3.6 g of 3-aminomethyl-4-(3-o-chlorobenzoyl-5-ethyl-2-thienyl)-5-methyl-4H-1,2,4-triazole di-paratoluenesulfonate as colorless needles melting at 167° – 170°C.

EXAMPLE 2

A solution of 5.0 g of 6-o-chlorophenyl-8-ethyl-4H-s-triazole[3,4-c]thieno[2,3-e][1,4]diazepine in 100 ml of 2.5% hydrochloric acid is stirred at 50° to 55°C for 4.5 hours. After cooling with ice, the reaction solution is neutralized with sodium bicarbonate. The oil liberated is extracted with ethyl acetate and the extract is dried over anhydrous sodium sulfate. To the extract is added a solution of 5.0 g of p-toluenesulfonic acid in methanol, and then the mixture becomes cloudy. Methonol is added in small portions to the mixture until the cloud disappears. The resulting clear solution is allowed to stand overnight in a refrigerator. The crystals formed are collected by filtration and recrystallized from a mixture of ethyl acetate and ethanol to give 4.5 g of 3-aminomethyl-4-(3-o-chlorobenzoyl-5-ethyl-2-thienyl)-4H-1,2,4-triazole di-paratoluenesulfonate as colorless pillars melting at 167° – 169°C.

EXAMPLE 3

A solution of 5 g of 1,8-dimethyl-6-o-chlorophenyl-4H-s-triazole[3,4-c]thieno[2,3-e][1,4]diazepine in 50 ml of 5% hydrochloric acid is refluxed for 4 hours. After cooling, the reaction solution is neutralized with sodium carbonate, and then the oil liberated is extracted with chloroform. 6.5 g of p-toluenesulfonic acid are dissolved in the chloroform layer, and the resulting solution is dried over anhydrous sodium sulfate. The chloroform is distilled off under reduced pressure, and the residue is treated with a mixture of ethyl acetate and ethanol to cause crystallization. The crystals are collected by suction filtration and recrystallized from a mixture of ethyl acetate and ethanol to give 3.8 g of 3-aminomethyl-4-(3-o-chlorobenzoyl-5-methyl-2-thienyl)-5-methyl-4H-1,2,4-triazole di-paratoluenesulfonate as colorless needles melting at 149° – 151°C.

EXAMPLE 4

In an identical manner as described in Example 3, 5.0 g of 1,7,8-trimethyl-6-o-chlorophenyl-4H-s-triazolo[3,4-c]thieno[2,3-e][1,4]diazepine is treated in 50 ml of 5% hydrochloric acid to give 4.8 g of 3-aminomethyl 4-(3-o-chlorobenzoyl-4,5-dimethyl-2-thienyl)-5-methyl-4H-1,2,4-triazole di-paratoluenesulfonate as colorless needles melting at 163° – 165°C.

EXAMPLE 5

A solution of 6.7 g of 6-o-chlorophenyl-8-ethyl-4H-imidazo[2,1-c]thieno[2,3-e][1,4]diazepine in a mixture of 10 ml of 90% formic acid and 17 ml of 37% formaldehyde is refluxed for 6 hours. After cooling, the reaction solution is poured into 300 ml of water and made alkaline with potassium carbonate. The oil liberated is extracted with ethyl acetate, and the extract is dried over anhydrous sodium sulfate. The extract is dissolved in ethanol containing 2.0 g of oxalic acid. The solution is allowed to stand for some time to cause crystallization. The crystals are collected by suction filtration and recrystallized from ethanol to give 5.8 g of 2-dimethylaminomethyl-1-(3-o-chlorobenzoyl-5-ethyl-2-thienyl)imidazole oxalte as colorless needles melting at 150° – 152°C. The corresponding free base is a pale yellow viscous oil.

EXAMPLE 6

A solution of 15.0 g of 1-methyl-6-o-chlorophenyl-8-ethyl-4H-s-triazolo[3,4-c]thieno[2,3-e][1,4]diazepine in a mixture of 27 ml of 80% formic acid and 45 ml of 37% formaldehyde is refluxed for 6 hours. After cooling, the solution is poured into 400 ml of water and made slightly alkaline with sodium hydroxide. The oil liberated is extracted with ethyl acetate, and the extract is dried over anhydrous sodium sulfate. To the extract is added a solution of 5.5 g of oxalic acid in ethanol, and the mixture is stirred. The crystals formed are collected by suction filtration and recrystallized from 95% ethanol to give 15.1 g of 3-dimethylaminomethyl-4-(3-o-chlorobenzoyl-5-ethyl-2-thienyl)-5-methyl-4H-1,2,4-triazole oxalate as colorless fine needles melting at 172° – 175°C. The corresponding free base is a pale yellow viscous oil.

EXAMPLE 7

To 7.3 g of 6-o-chlorophenyl-8-ethyl-4H-tetrazolo[5,1-c]thieno[2,3-e][1,4]diazepine is added a mixture of 12.3 ml of 90% formic acid and 21.3 ml of 37% formaldehyde, and the whole mixture is heated under reflux for 6 hours. After cooling, the reaction mixture is poured into 400 ml of water and made alkaline with potassium carbonate. The oil liberated is extracted with ethyl acetate and the extract is dried over anhydrous sodium sulfate. To the extract is added 2.0 g of oxalic acid dissolved in ethanol, and the mixture is stirred. The crystals formed are collected by suction filtration and recrystallized from 90% ethanol to give 6.5 g of 1-(3-o-chlorobenzoyl-5-ethyl-2-thienyl)-5-dimethylaminomethyl-tetrazole oxalate as colorless crystalline powder melting at 170° – 171°C.

EXAMPLE 8

A solution of 8.1 g of 3-aminomethyl-4-(3-o-chlorobenzoyl-5-ethyl-2-thienyl)-5-methyl-4H-1,2,4-triazole di-paratoluenesulfonate in a mixture of 9 ml of 90% formic acid and 15 ml of 37% formaldehyde is refluxed for 5 hours. After cooling, the solution is poured into 150 ml of ice water and made alkaline with sodium carbonate. The oil liberated is extracted with ethyl acetate and the extract is dried over anhydrous sodium sulfate. To the extract is added 2.0 g of oxalic acid dissolved in ethanol, and the mixture is stirred. The crystals formed are collected by suction filtration and recrystallized from 90% ethanol to give 5.2 g of 3-dimethylaminomethyl-4-(3-o-chlorobenzoyl-5-ethyl-2 -thienyl)-5-methyl-4H-1,2,4-triazole oxalate melting at 172° – 175°C.

EXAMPLE 9

A solution of 3.0 g of 6-phenyl-8-ethyl-4H-s-triazolo[3,4-c]thieno[2,3-e][1,4]diazepine in a mixture of 5 ml of 90% formic acid and 7 ml of 37% formaldehyde is refluxed for 9 hours. After cooling, the solution is poured into 100 ml of water and made alkaline with potassium carbonate. The oil liberated is extracted with ethyl acetate and the extract is dried over anhydrous sodium sulfate. To the extract is added 2.0 g of oxalic acid dissolved in ethanol, and the mixture is allowed to stand. The crystals formed are collected by suction filtration and recrystallized from 95% ethanol to give 3.4 g of 3-dimethylaminomethyl-4-(3-benzoyl-5-ethyl-2-thienyl)-5-hydroxymethyl-4H-1,2,4-triazole oxalate as colorless crystalline powder melting at 176° – 177°C.

EXAMPLE 10 to 31

Other examples of compounds (I) ($R^3$ being $-N(CH_3)_2$) and acid addition salts thereof which can be produced from the corresponding compound of formula (IV) or (V) and a mixture of formic acid and formaldehyde in a manner similar to that described in Examples 5 to 9 are as follows:

EXAMPLE 32

To a solution of 4 g of 3-chloromethyl-4-(3-o-chlorobenzoyl-5-ethyl-2-thienyl)-5-methyl-4H-1,2,4-triazole in 20 ml of ethanol is added 12 ml of ethanol containing 30% dimethylamine, and the mixture is allowed to stand overnight at room temperature. After the removal of the solvent by the fractional distillation, water is added to the residue. The residue is made alkaline with potassium carbonate and extracted with ethyl acetate. The extract is washed with water and dried over anhydrous sodium sulfate. The solvent is distilled off and the residue is allowed to react with 0.9 g of anhydrous oxalic acid in ethanol. The resulting crude crystals are recrystallized from ethanol to give 4.1 g of 3-dimethylaminomethyl-4-(3-o-chlorobenzoyl-5-ethyl-2-thienyl)-5-methyl-4H-1,2,4-tirazole oxalate as colorless crystals melting at 172° – 175°C (decomposition).

EXAMPLE 33

To a suspension of 7 g of 3-tosyloxymethyl-4-(3-o-chlorobenzoyl-5-ethyl-2-thienyl)-5-methyl-4H-1,2,4-triazole in 100 ml of ethanol is added 2 g of N-methylpiperazine, and the mixture is refluxed for 5 hours. Aftr the completion of the reaction, the solvent is distilled off and water is added to the residue. The residue is made alkaline with potassium carbonate and extracted with ethyl acetate. The extract is washed with water and dried over anhydrous sodium sulfate. The solvent is distilled off and the residue obtained is allowed to react with 2.2 g of oxalic acid in ethanol. The crude crystals formed are recrystallized from aqueous ethanol to give 3.8 g of 3-(4-methyl-1-piperazinylmethyl)-4-(3-o-chlorobenzoyl-5-ethyl-2-thienyl)-5-methyl-4H-1,2,4-triazole dioxalate ½ hydrate as colorless crystals melting at 164° – 165°C (decomposition).

EXAMPLE 34

To a solution of 7.3 g of 2-chloromethyl-1-(3-o-chlorobenzoyl-5-ethyl-2-thienyl)imidazole in 20 ml of a 25% dimethylamine solution in ethanol, and the mixture is stirred for 8 hours at room temperature. After

| Example | A | B | $R^1$ | $R^2$ | X | Melting Point (°C) |
|---|---|---|---|---|---|---|
| 10 | CH | CH | H | $CH_3$ | o-Cl | oxalate 143 – 145 |
| 11 | CH | CH | H | $C_2H_5$ | H | oxalate 172 – 175 (decomposition) |
| 12 | CH | CH | H | $C_2H_5$ | p-Cl | oxalate 165 – 167 |
| 13 | CH | CH | H | $C_2H_5$ | o-F | oxalate 167 – 168 |
| 14 | CH | CH | H | $C_2H_5$ | p-F | oxalate 169 – 171 (decomposition) |
| 15 | CH | CH | H | $C_2H_5$ | o-Br | oxalate 140 – 141 |
| 16 | CH | CH | H | $C_2H_5$ | p-$OCH_3$ | oxalate 173 – 174 |
| 17 | CH | CH | $CH_3$ | $CH_3$ | o-Cl | oxalate 170 – 171 |
| 18 | CH | CH | —$(CH_2)_4$— | | H | oxalate 174 – 176 (decomposition) |
| 19 | CH | CH | —$(CH_2)_4$— | | o-Cl | oxalate 176 – 177 (decomposition) |
| 20 | C—$CH_3$ | CH | H | $C_2H_5$ | o-Cl | base 98 – 100 |
| 21 | CH | N | H | $C_2H_5$ | o-Cl | oxalate 1/2 $H_2O$ 160–161 (decomposition) |
| 22 | C—$CH_3$ | N | H | $CH_3$ | o-Cl | oxalate 174 – 176 |
| 23 | C—$CH_3$ | N | H | $C_2H_5$ | p-Cl | base 150 – 152 |
| 24 | C—$CH_3$ | N | H | $C_2H_5$ | o-Br | oxalate 168 – 170 |
| 25 | C—$CH_3$ | N | H | $C_2H_5$ | o-F | oxalate 169 – 170 (decomposition) |
| 26 | C—$CH_3$ | N | H | $C_2H_5$ | p-F | base 107 – 108 |
| 27 | C—$CH_3$ | N | $CH_3$ | $CH_3$ | o-Cl | base 145 – 146 |
| 28 | C—$CH_3$ | N | —$(CH_2)_4$— | | o-Cl | oxalate 179 – 181 (decomposition) |
| 29 | C—$CH_2OH$ | N | H | $C_2H_5$ | o-Cl | oxalate 144 – 146 (decomposition) |
| 30 | N | N | H | $C_2H_5$ | o-Cl | oxalate 170 – 171 |
| 31 | N | N | $CH_3$ | $CH_3$ | o-Cl | oxalate 189 – 190 |

15 allowing the mixture to stand overnight, the solvent is distilled off under reduced pressure. The residue to which a water is added is extracted with chloroform, and the extract was washed with water and dried over anhydrous magnesium sulfate. The chloroform is distilled off under reduced pressure. The residual brown oil is dissolved in ethyl acetate, and a stoichiometric quantity of anhydrous oxalic acid is added to the solution. The crystals formed are recrystallized from ethanol to give 2-dimethylaminomethyl-1-(3-o-chlorobenzoyl-5-ethyl-2-thienyl)imidazole oxalate as colorless crystals melting at 150° – 152°C.

EXAMPLE 35

To a solution of 5.6 g of 2-chloromethyl-1-(3o-chlorobenzoyl-5-ethyl-2-thienyl)imidazole in 50 ml of ethanol is added 4 g of diethylamine, and the mixture is stirred at 50°C for 2 hours. After allowing the mixture to stand overnight, the solvent is distilled off under reduced pressure. The residue to which a water is added is extracted with ethyl acetate. The extract is washed with water and dried over anhydrous magnesium sulfate. The solvent is distilled off under reduced pressure. The residual brown oil is chromatographed on 150 g of 70 – 325 mesh silica gel with chloroform as eluent. The eluates are combined and concentrated in vacuo to give 2-diethylaminomethyl-1-(3-o-chlorobenzoyl-5-ethyl-2-thienyl)imidazole as yellowish transparent oil ($n_D^{21}$ = 1.5813).

EXAMPLE 36

To a solution of 3.5 g of 2-chloromethyl-1-(3-o-chlorobenzoyl-5-ethyl-2-thienyl)imidazole in 35 ml of toluene is added 2.2 g of piperidine, and the mixture is refluxed for 2 hours. After cooling, the piperidine hydrochloride precipitate is removed by filtration. The filtrate is dried over anhydrous magnesium sulfate and the solvent is distilled off under reduced pressure. The residual brown oil is dissolved in ethyl acetate, and to the solution is added a stoichiometric amount of anhydrous oxalic acid. The crystals formed are collected by filtration and recrystallized from a mixture of ethyl acetate and ethanol to give 2-piperidinomethyl-1-(3-o-chlorobenzoyl-5-ethyl-2-thienyl)-imidazole oxalate as colorless crystals melting at 145° – 146°C.

EXAMPLES 37 to 46

Proceeding by the method of Example 32 to 36, but substituting equivalent amounts of appropriate starting materials, the compounds identical to the products of above Example 1 to 31 are also produced, other compounds which can be produced in this manner include the following:

| Example | A | B | R¹ | R² | R³ | X | Melting Point (°C) |
|---------|------|----|----|-------|--------------------|------|------------------------------|
| 37 | CH | CH | H | C₂H₅ | —N(H)(CH₃) | o-Cl | oxalate 162 – 163 |
| 38 | CH | CH | H | C₂H₅ | —N(H)(CH(CH₃)₂) | o-Cl | oxalate 146 – 147 |
| 39 | CH | CH | H | C₂H₅ | —N(H)(C₆H₁₁) | o-Cl | oxalate 172 – 173 |
| 40 | CH | CH | H | C₂H₅ | —N(pyrrolidinyl) | o-Cl | oxalate 184 – 185 |
| 41 | CH | CH | H | C₂H₅ | —N(piperazinyl)—CH₃ | o-Cl | oxalate 188 – 189 |
| 42 | CH | CH | H | C₂H₅ | —N(morpholinyl) | o-Cl | oxalate 145 – 146 |
| 43 | C—CH₃ | N | H | C₂H₅ | —N(H)(CH₃) | o-Cl | oxalate 183 – 184 (decomposition) |
| 44 | C—CH₃ | N | H | C₂H₅ | —N(pyrrolidinyl) | o-Cl | base 94 – 95 |
| 45 | C—CH₃ | N | H | C₂H₅ | —N(piperidinyl) | o-Cl | dihydrochloride 202 – 204 (decomposition) |
| 46 | C—CH₃ | N | H | CH₃ | —N(morpholinyl) | o-Cl | oxalate 178 – 179 (decomposition) |

While the invention has been described in detail and with reference to specific embodiments thereof, it will be apparent to one skilled in the art that various changes and modifications can be made therein without departing from the spirit and scope thereof.

What is claimed is:

1. A compound selected from the group consisting of a compound of the formula:

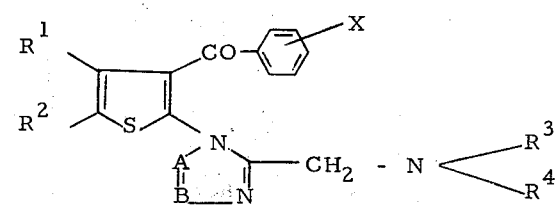

and a pharmaceutically acceptable acid addition salt thereof, wherein R¹ is H or CH₃; R² is CH₃ or C₂H₅;

each of $R^3$ and $R^4$ is H, alkyl of from 1 to 4 carbon atoms or cyclohexyl, or $R^3$ and $R^4$ together with the adjacent nitrogen atom form 1-pyrrolidinyl, piperidino, 4-methyl-1-piperazinyl or morpholino; X is H, halogen or $OCH_3$; A is —CH= or —C($CH_3$)=; and B is =CH—.

2. A compound according to claim 1, said compound being 1-(3-o-chlorobenzoyl-5-ethyl-2-thienyl)-2-dimethylaminomethylimidazole.

3. A compound according to claim 1, said compound being 1-(5-ethyl-3-o-fluorobenzoyl-2-thienyl)-2-dimethylaminomethylimidazole.

4. A compound according to claim 1, said compound being 1-(3-o-bromobenzoyl-5-ethyl-2-thienyl)-2-dimethylaminomethylimidazole.

5. A compound according to claim 1, said compound being 1-(3-o-chlorobenzoyl-5-ethyl-2-thienyl)-2-dimethylaminomethyl-5-methylimidazole.

6. A compound according to claim 1, said compound being 1-(3-benzoyl-5-ethyl-2-thienyl)-2-dimethylaminomethylimidazole.

* * * * *